United States Patent [19]
Amagi et al.

[11] Patent Number: 5,945,504
[45] Date of Patent: Aug. 31, 1999

[54] EPISULFIDE COMPOUND

[75] Inventors: Akikazu Amagi, Tokyo; Nobuyuki Uemura, Chiba-ken; Motoharu Takeuchi, Tokyo; Kenichi Takahashi, Chiba-ken; Minoru Ohashi, Chiba-ken; Hiroshi Horikoshi, Chiba-ken; Masanori Shimuta, Tokyo, all of Japan

[73] Assignee: Mitsubishi Gas Chemical Company, Inc., Tokyo, Japan

[21] Appl. No.: 08/782,720

[22] Filed: Jan. 13, 1997

[30] Foreign Application Priority Data

Jan. 17, 1996 [JP] Japan ................................. 8-005797

[51] Int. Cl.⁶ .................................................. C08G 75/08
[52] U.S. Cl. .............................. 528/373; 528/96; 528/99; 528/380; 528/393
[58] Field of Search ..................... 528/380, 373, 528/96, 99, 393

[56] References Cited

U.S. PATENT DOCUMENTS 5,182,340  1/1993  Hefner et al. .

FOREIGN PATENT DOCUMENTS 1 252 717  11/1971  United Kingdom .

OTHER PUBLICATIONS

Chemicals Abstracts, vol. 115, No. 37, 1991, Columbus, Ohio, Abstract No. 137564z, p. 57, col. 2, XP002028341 of JP 00 381 321 A (Mitsui Toatsu Chemicals).

*Primary Examiner*—Robert Dawson
*Assistant Examiner*—D. Aylward
*Attorney, Agent, or Firm*—Frishauf, Holtz, Goodman, Langer & Chick, P.C.

[57] ABSTRACT

An episulfide which has an alicyclic, aromatic or heterocyclic skeleton and has two or more moieties represented by the formula

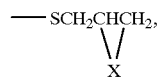

wherein X is S or O, and S is in an amount of 50% or more, on the average, of the total of S and O constituting a three-membered ring. A cured material obtained by polymerizing this episulfide compound is a desirable optical material for various uses, particularly as a lens material for spectacles.

17 Claims, No Drawings

EPISULFIDE COMPOUND

BACKGROUND OF THE INVENTION

1. Field of the Invention

The present invention relates to a novel episulfide compound. More specifically, the present invention relates to a novel episulfide compound which can suitably be used as an optical material for plastic lenses, prisms, optical fibers, information recording substrates, filters and the like, above all, a material for plastic spectacle lenses.

2. Description of the Related Art

Plastic materials are lightweight, tough and easily dyeable, and for this reason, they have often been used as various optical materials, particularly spectacle lenses in recent years. As the performance of the optical materials, particularly the spectacle lenses, they are required to possess a low specific gravity, optical performances such as a high refractive index and a high Abbe's number, and physical performances such as a high heat resistance and a high strength. The high refractive index permits the lenses to be thin, the high Abbe's number decreases the chromatic aberration of the lenses, and the high heat resistance and the high strength can facilitate the secondary processing of the lenses and they are also important from the viewpoints of safety and the like. Typical plastic materials at an early stage of conventional techniques in this field are materials obtained by polymerizing compounds such as diethylene glycol bis-allyl carbonate, a combination of this bisallyl carbonate and diallyl phthalate, and various kinds of methacrylates. These plastic materials have a refractive index of about 1.5 to 1.55, so that the obtained lenses are thick, and in consequence, the lightweight properties are lost. Therefore, the materials having the high refractive index have been desired, and various investigations have been conducted with the intention of obtaining a refractive index of 1.6 or more. There have already been suggested a polymer of a methacrylate compound containing a chlorine atom or a bromine atom, and a thermosetting optical material having a urethane structure obtained by the reaction of a hydroxy compound containing the bromine atom with an isocyanate (Japanese Patent Application Laid-open No. 164615/1983 and the like). However, when the compound containing the chlorine atom or the bromine atom is used, the specific gravity of the obtained lenses is large, and also in this case, the lightweight properties are eventually lost. Thus, thermosetting optical materials having thiourethane structures obtained by the reaction of polythiol compounds with polyisocyanate compounds have been suggested in Japanese Patent Publication No. 58489/1992 and Japanese Patent Application Laid-open No. 148340/1993. The various novel polythiol compounds which can be used as the materials of these thiourethanes have also been suggested. That is to say, Japanese Patent Application Laid-open No. 148340/1993 has suggested a branched polythiol compound having 4 sulfur atoms in one molecule; Japanese Patent Application Laid-open No. 270859/1990 has suggested a branched polythiol compound having 5 sulfur atoms in one molecule; and Japanese Patent Application Laid-open No. 192250/1994 has suggested a polythiol compound having a dithiane ring structure in one molecule. Additionally, in Japanese Patent Laid-open No. 81320/1991, there has been suggested a process for preparing a lens material by the use of a compound obtained by converting, into an episulfide group, a part or all of the epoxy groups of each of epoxy compounds such as known amine epoxy resins, phenolic epoxy resins, alcoholic epoxy resins, unsaturated compounds-containing epoxy resins, glycidyl ester epoxy resins, urethane epoxy resins and alicyclic epoxy resins. The thiourethane resin lenses which can be obtained by the polythiol compounds and the polyisocyanate compounds can possess a refractive index as high as about 1.66. However, episulfide resin lenses which can be obtained from episulfide compounds derived from known epoxy resins have a refractive index of at most about 1.6. Anyway, the problems of further thinning and reducing the weight of lenses can be solved to some extent by these conventional sulfur-containing compounds, but needless to say, a further higher refractive index is desirable. On the other hand, another important performance required for the optical material is that the chromatic aberration is low. The higher the Abbe's number is, the lower this chromatic aberration is, and therefore a material having the high Abbe's number is desired. That is to say, the simultaneous achievement of a high refractive index and a high Abbe's number is also desired. However, the Abbe's number usually tends to decline with an increase in the refractive index, and in plastic materials obtained by using conventional diethylene glycol bisallyl carbonate, known episulfide compounds and conventional compounds such as the polythiol compounds and the polyisocyanate compounds as raw materials, the Abbe's number is in the range of about 50 to 55 in the case of a refractive index of 1.5 to 1.55, and it is about 40 in the case of a refractive index of 1.60 and it is at most about 32 in the case of a refractive index of 1.66. On the other hand, the improvement of the heat resistance has often been tried by the use of a polyfunctional compound and a crosslinking agent, but in general, for the expression of a high refractive index, the molecular weight of the material compound is increased, so that the crosslink density decreases. For the expression of a high Abbe's number, the alkyl group content is increased, so that the stiffness of molecules constituting the material compound deteriorates and a sufficient improvement effect has not been obtained yet.

In the conventional optical materials obtained from the episulfide compounds and the combinations of the polythiol compounds and the isocyanate compounds, the increase in the refractive index is limited, and this increase in the refractive index leads to the deterioration of the Abbe's number. Therefore, there has been a problem that the sufficiently high refractive index and Abbe's number cannot be balanced with each other. Furthermore, the improvement of the above-mentioned optical properties, i.e., the refractive index and the Abbe's number leads to the deterioration of the heat resistance, and therefore there has been a problem that while the sufficiently high refractive index and Abbe's number are balanced with each other, the excellent heat resistance cannot be obtained.

SUMMARY OF THE INVENTION

An object of the present invention is to provide a novel sulfur-containing compound which can become an optical material having a small thickness and a low chromatic aberration.

Another object of the present invention is to provide a novel sulfur-containing compound which can become an optical material having a small thickness, a low chromatic aberration and a high heat resistance.

Still another object of the present invention is to provide a novel optical material having such excellent optical properties as mentioned above.

The present invention is directed to an episulfide compound having two or more moieties represented by the following formula (1) and having a cyclic skeleton

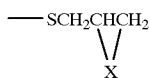   (1)

wherein X is S or O, and a numerical ratio of S is 50% or more, on the average, of the total of S and O constituting a three-membered ring.

The episulfide compound having two or more moieties represented by the formula (1) and having the cyclic skeleton can typically roughly classified into (a) an episulfide compound in which the cyclic skeleton is an alicyclic skeleton, (b) an episulfide compound in which the cyclic skeleton is an aromatic skeleton, and (c) an episulfide compound in which the cyclic skeleton is a heterocyclic skeleton including a sulfur atom as a hetero-atom.

Furthermore, each of these compounds may contain a linkage of a sulfide, an ether, a sulfone, a ketone, an ester or the like.

Preferable and typical examples of the episulfide compound (a) having the alicyclic skeleton include 1,3- and 1,4-bis(β-epithiopropylthio)cyclohexane, 1,3- and 1,4-bis(β-epithiopropylthiomethyl)cyclohexane, bis[4-(β-epithiopropylthio)cyclohexyl]methane, 2,2-bis[4-(β-epithiopropylthio)cyclohexyl]propane, bis[4-(β-epithiopropylthio)cyclohexyl]sulfide, 2,5-bis(β-epithiopropylthio)-1,4-dithiane, and 2,5-bis(β-epithiopropylthioethylthiomethyl)-1,4-dithiane.

Preferable and typical examples of the episulfide compound (b) having the aromatic skeleton include 1,3- and 1,4-bis(β-epithiopropylthio)benzene, 1,3- and 1,4-bis(β-epithiopropylthiomethyl)benzene, bis[4-(β-epithiopropylthio)phenyl]methane, 2,2-bis[4-(β-epithiopropylthio)phenyl]propane, bis[4-(β-epithiopropylthio)phenyl]sulfide, bis[4-(β-epithiopropylthio)phenyl]sulfone, and 4,4-bis(β-epithiopropylthio)biphenyl.

Examples of the episulfide compound (c) having the heterocyclic skeleton including the sulfur atom as the hetero-atom include episulfide compounds having a structure represented by the formula (2)

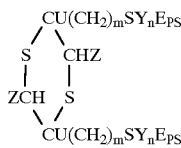   (2)

wherein $E_{ps}$ is an epithiopropyl group represented by the following formula (3); Y is $-(CH_2CH_2S)$; Z is a hydrogen atom, an alkyl group having 1 to 5 carbon atoms or $-(CH_2)_mSY_nE_{ps}$; U is a hydrogen atom or an alkyl group having 1 to 5 carbon atoms; m is an integer of 1 to 5; and n is an integer of 0 to 4,

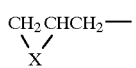   (3)

wherein X is S or O, and a numerical ratio of S is 50% or more, on the average, of the total of S and O constituting a three-membered ring.

In the formula (2), n is an integer of 0 to 4, preferably 0 to 3, more preferably 0 to 2, most preferably 0. Moreover, m is an integer of 1 to 5, preferably 1 to 4, more preferably 1 to 3, most preferably 1. In the formula (3), X is S or O, and a numerical ratio of S is 50% or more, on the average, of the total of S and O constituting the three-membered ring, and it is preferably 80 to 100%, more preferably 90 to 100%, particularly preferably 95 to 100%, most preferably 100%. If n is more than 4, the heat resistance of an optical material obtained by polymerization/curing is too poor to be used as the optical material. Furthermore, even if n is 4 or less, the smaller it is, the more advantageous it is from the viewpoint of the heat resistance, but the larger it is, the more advantageous it is from the viewpoint of the flexibility of the material. When m is 4 or 5, the content of sulfur is low, so that a high refractive index cannot be attained and the heat resistance of the material deteriorates. A case where m is 1 is most advantageous from the viewpoints of the refractive index and the heat resistance. In the formula (3), if the numerical ratio of S in X is 80% or more, particularly 50% or less, on the average, of the total of S and O constituting the three-membered ring, the content of sulfur is low, so that a high refractive index cannot be attained, and the reactivity of the compound lowers, which requires the polymerization at a high temperature. In consequence, the material tends to be colored. The performance of the compound according to the present invention and the optical material obtained by its polymerization/curing depends upon the integers n and m as well as the ratio of S in X, as described above. However, in preferable embodiments and the like, the integers n and m are not independently decided within the above-mentioned ranges. Preferable examples include compounds in which n is in the range of 0 to 3 and m is in the range of 1 to 4. Above all, the compounds in which n is in the range of 0 to 2 and m is in the range of 1 to 3 are more preferable. Among others, the compounds in which n is 0 and m is 1 are most preferable. In addition, U is any of the hydrogen atom and the alkyl groups having 1 to 5 carbon atoms, but in order to maintain the refractive index at a high level, the hydrogen atom is preferable. Z is any of the hydrogen atom, the alkyl groups having 1 to 5 carbon atoms and $-(CH_2)_mSY_nE_{ps}$, but from the viewpoint of the high heat resistance, $-(CH_2)_mSY_nE_{ps}$ for increasing a crosslink density is desirable, but in consideration of balance between the heat resistance and the flexibility of the material, the hydrogen atom is more preferable.

Of these compounds, some examples will actually be enumerated. That is to say, they include 2,5-bis(β-epithiopropylthiomethyl)-1,4-dithiane, 2,5-bis(β-epithiopropylthioethylthiomethyl)-1,4-dithiane, 2,5-bis(β-epithiopropylthioethyl)-1,4-dithiane and 2,3,5-tri(β-epithiopropylthioethyl)-1,4-dithiane:

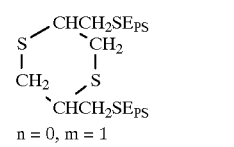

n = 0, m = 1

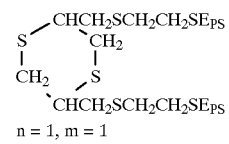

n = 1, m = 1

-continued

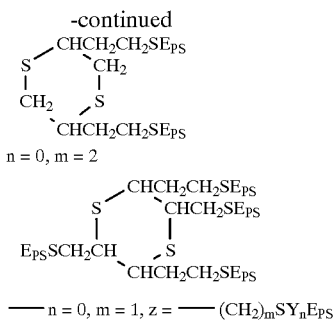

n = 0, m = 2

$$S\begin{matrix}CHCH_2CH_2SE_{PS}\\CHCH_2SE_{PS}\end{matrix}$$

$$E_{PS}SCH_2CH\begin{matrix}S\\CHCH_2CH_2SE_{PS}\end{matrix}\begin{matrix}CHCH_2SE_{PS}\\S\end{matrix}$$

—— n = 0, m = 1, z = —— $(CH_2)_m SY_n E_{PS}$

The optical material of the cured resin according to the present invention may be obtained by copolymerizing/curing any of one and mixtures of the materials (a), (b) and (c), so long as it is suitable for the objects of the present invention.

The novel episulfide compound of the present invention represented by the formula (1) can be prepared by any of various methods, but for example, by a method which comprises reacting a compound of the formula (4) having two or more mercapto groups corresponding to the compound (a), (b) or (c) with an epihalohydrin typified by epichlorohydrin in the presence of an alkali to obtain a compound having an epoxy group represented by the formula (5), and then reacting the thus obtained epoxy compound with a thia-compound forming agent such as a thiocyanate, thiourea, triphenylphosphine sulfide or 3-methylbenzothiazole-2-thione, preferably the thiocyanate or thiourea:

wherein n is an integer of 2 or more; and R is a compound having a cyclic structure having 1 to 20 carbon atoms, and this compound may contain a linkage of a sulfide, an ether, a sulfone, an ester, a ketone or the like.

In the preparation method of the epoxy compound represented by the formula (5), epichlorohydrin is preferable as the epihalohydrin compound. Furthermore, the epihalohydrin compound is stoichiometrically used in an amount of moles corresponding to the number of the mercapto groups of the mercaptan compound represented by the formula (4), but if the purity, the reaction rate, the economy and the like of the product are regarded as important, the amount of the epihalohydrin compound may be less than or more than the above-mentioned moles. For the reaction, the epihalohydrin compound can be used preferably in the range of from its stoichiometric amount to 5 times as much as the stoichiometric amount in terms of mol, more preferably in the range of from the stoichiometric amount to 2.5 times as much as the stoichiometric amount in terms of mol. The reaction may be carried out under non-solvent conditions or in a solvent, but when the solvent is used, it is preferable to use the solvent which can dissolve any of the epihalohydrin, the mercaptan compound of the formula (4) and a metallic salt of the mercaptan compound. Typical examples of the solvent include water, alcohols, ethers, aromatic hydrocarbons, halogenated hydrocarbons and mixtures thereof. The reaction can easily proceed in the presence of the stoichiometric amount or more of a base. Examples of the base include pyridine, tertiary amines such as triethylamine and diazabicycloundecene, and hydroxides of alkali metals and alkaline earth metals. Above all, the hydroxides of the alkali metals and the alkaline earth metals are preferable, and sodium hydroxide, potassium hydroxide and the like are more preferable. A reaction temperature is usually in the range of 0 to 100° C., preferably 0 to 60° C. A reaction time is a time taken to complete the reaction under the selected requirements of the above-mentioned various conditions, but the proper reaction time is usually 10 hours or less.

In the preparation method of the novel episulfide compound of the present invention from the epoxy compound represented by the formula (5), the thiocyanate can be used as the thia-compound forming agent, but in this case, examples of the preferable thiocyanate include salts of alkali metals and alkaline earth metals, and potassium thiocyanate and sodium thiocyanate are more preferable. Furthermore, the thiocyanate or thiourea which is the thia-compound forming agent can be stoichiometrically used in an amount of moles corresponding to the number of the epoxy groups of the epoxy compound represented by the formula (2), but if the purity, the reaction rate, the economy and the like of the product are regarded as important, the amount of the thiocyanate or thiourea may be less than or more than the above-mentioned moles. For the reaction, the thiocyanate or thiourea can be used preferably in the range of from its stoichiometric amount to 5 times as much as the stoichiometric amount in terms of mol, more preferably in the range of from the stoichiometric amount to 2.5 times as much as the stoichiometric amount in terms of mol. The reaction may be carried out under non-solvent conditions or in a solvent, but when the solvent is used, it is preferable to use the solvent which can dissolve any of the thiocyanate, thiourea and the epoxy compound of the formula (5). Typical examples of the solvent include water, alcohols such as methanol and ethanol; ethers such as diethyl ether, tetrahydrofuran and dioxane; hydroxyethers such as methyl cellosolve, ethyl cellosolve and butyl cellosolve; aromatic hydrocarbons such as benzene, toluene and xylene; and halogenated hydrocarbons such as dichloroethane, chloroform and chlorobenzene. Some combinations of these solvents, for example, a combination of the alcohol and water, and a combination of the ether, hydroxyether, the halogenated hydrocarbon or the aromatic hydrocarbon and the alcohol are effective on occasion. In addition, it is an effective means for the enhancement of reaction results to add an acid, an acid anhydride or the like as a polymerization inhibitor to a reaction solution. Typical examples of the acid, the acid anhydride and the like include nitric acid, hydrochloric acid, sulfuric acid, fuming sulfuric acid, boric acid, arsenic acid, phosphoric acid, prussic acid, acetic acid, peracetic acid, thioacetic acid, oxalic acid, tartaric acid, propionic acid, butyric acid, succinic acid, maleic acid, benzoic acid, anhydrous nitric acid, anhydrous sulfuric acid, boron oxide, arsenic pentoxide, phosphorus pentoxide, chromic anhydride, acetic anhydride, propionic anhydride, butyric anhydride, succinic anhydride, maleic anhydride, benzoic anhydride, phthalic anhydride, silica gel, silica alumina and aluminum chloride, and they may be used singly or in a combination thereof. The amount of the acid, the acid anhydride or the like to be used is usually in the range of 0.001 to 10% by weight, preferably 0.01 to 1% by weight with respect to the total amount of the reaction solution. A reaction temperature is usually in the range of 0 to 100° C., preferably 20 to 70° C. A reaction time is a time taken to complete the reaction under the selected requirements of the above-mentioned various conditions, but the proper reaction time is usually 20 hours or less. When the reaction product is washed with an aqueous acidic solution, the stability of the obtained compound can be improved. Typical examples of the acid which can be used for the aqueous acidic solution include nitric acid, hydrochloric acid, sulfuric acid, boric acid, arsenic acid, phosphoric acid, prussic acid, acetic acid, peracetic acid, thioacetic acid, oxalic acid, tartaric acid, succinic acid and maleic acid, and they may be used singly or in a mixture of two or more thereof. The aqueous solution of each of these acids can usually exert the effect when it is at a pH of 6 or less, but the more effective pH is in the range of 3 to 0.

As a method other than described above, there is a method which comprises producing the epoxy compound of the formula (5) by oxidizing a corresponding unsaturated compound of the following formula (6) with an organic peracid, an alkyl hydroperoxide, hydrogen peroxide or the like, and then carrying out the above-mentioned manner to prepare the episulfide compound having two or more moieties represented by the formula (1) and having the cyclic skeleton:

$$R(-SCH_2CH=CH_2)_n \qquad (6)$$

wherein X is a chlorine atom or a bromine atom; and R and n are as defined in the case of the formula (4).

As still another method, there is a useful method for preparing the episulfide compound from a halomercaptan compound represented by the formula (7) in accordance with a dehalogenation hydrogen reaction. It is known that the halomercaptan can easily be synthesized from the above-mentioned unsaturated compound and sulfur chloride or the like [e.g., F. Lautenschlaerger et al., "J. Org. Chem.", 34, p. 396 (1969)]:

$$R(-SCH_2CHSHCH_2X)_n \qquad (7)$$

wherein X is a chlorine atom or a bromine atom; and R and n are as defined in the case of the formula (4).

The novel episulfide compound of the present invention can be heated and polymerized in the presence or absence of a curing catalyst to prepare a cured resin which is advantageous for an optical material and the like. A preferable method for the preparation of the cured resin is a process in which the curing catalyst is used, and examples of the usable curing catalyst include amines, phosfines, mineral acids, Lewis acids, organic acids, silicates and tetrafluoroboric acid. Typical examples of the curing catalyst include (1) amine compounds typified by primary amines such as ethylamine, n-propylamine, sec-propylamine, n-butylamine, sec-butylamine, iso-butylamine, tert-butylamine, pentylamine, hexylamine, heptylamine, octylamine, decylamine, laurylamine, myristylamine, 1,2-dimethylhexylamine, 3-pentylamine, 2-ethylhexylamine, allylamine, aminoethanol, 1-aminopropanol, 2-aminopropanol, aminobutanol, aminopentanol, aminohexanol, 3-ethoxypropylamine, 3-propoxypropylamine, 3-isopropoxypropylamine, 3-butoxypropylamine, 3-isobutoxypropylamine, 3-(2-ethylhexyloxy)propylamine, aminocyclopentane, aminocyclohexane, aminonorbornene, aminomethylcyclohexane, amonobenzene, benzylamine, phenethylamine, α-phenylethylamine, naphthylamine and furfurylamine; primary polyamines such as ethylenediamine, 1,2-diaminopropane, 1,3-diaminopropane, 1,2-diaminobutane, 1,3-diaminobutane, 1,4-diaminobutane, 1,5-diaminopentane, 1,6-diaminohexane, 1,7-diaminoheptane, 1,8-diaminooctane, dimethylaminopropylamine, diethylaminopropylamine, bis-(3-aminopropyl)ether, 1,2-bis-(3-aminopropoxy)ethane, 1,3-bis-(3-aminopropoxy)-2,2'-dimethylpropane, amonoethylethanolamine, 1,2-bisaminocyclohexane, 1,3-bisaminocyclohexane, 1,4-bisaminocyclohexane, 1,3-bisaminomethylcyclohexane, 1,4-bisaminomethylcyclohexane, 1,3-bisaminoethylcyclohexane, 1,4-bisaminoethylcyclohexane, 1,3-bisaminopropylcyclohexane, 1,4-bisaminopropylcyclohexane, hydrogenated 4,4'-diamonodiphenylmethane, 2-aminopiperidine, 4-aminopiperidine, 2-aminomethylpiperidine, 4-aminomethylpiperidine, 2-aminoethylpiperidine, 4-aminoethylpiperidine, N-aminoethylpiperidine, N-aminopropylpiperidine, N-aminoethylmorpholine, N-aminopropylmorpholine, isophoronediamine, methanediamine, 1,4-bisaminopropylpiperazine, o-phenylenediamine, m-phenylenediamine, p-phenylenediamine, 2,4-tolylenediamine, 2,6-tolylenediamine, 2,4-toluenediamine, m-aminobenzylamine, 4-chloro-o-phenylenediamine, tetrachloro-p-xylylenediamine, 4-methoxy-6-methyl-m-phenylenediamine, m-xylylenediamine, p-xylylenediamine, 1,5-naphthalenediamine, 2,6-naphthalenediamine, benzidine, 4,4'-bis(o-toluidine), dianisidine, 4,4'-diaminodiphenylmethane, 2,2-(4,4'-diaminodiphenyl) propane, 4,4'-diamino diphenyl ether, 4,4'-thiodianiline, 4,4'-diaminodiphenylsulfone, 4,4'-diaminoditolylsulfone, methylenebis(o-chloroaniline), 3,9-bis(3-aminopropyl)-2,4,8,10-tetraoxaspiro[5.5]undecane, diethylenetriamine, iminobispropylamine, methyliminobispropylamine, bis(hexamethylene)triamine, triethylenetetramine, tetraethylenepentamine, pentaethylenehexamine, N-aminoethylpiperazine, N-aminopropylpiperazine, 1,4-bis(aminoethylpiperazine), 1,4-bis(aminopropylpiperazine), 2,6-diaminopyridine and bis(3,4-diaminophenyl)sulfone; secondary amines such as diethylamine, dipropylamine, di-n-butylamine, di-sec-butylamine, diisobutylamine, di-n-pentylamine, di-3-pentylamine, dihexylamine, octylamine, di(2-ethylhexyl)amine, methylhexylamine, diallylamine, pyrrolidine, piperidine, 2-picoline, 3-picoline, 4-picoline, 2,4-lupetidine, 2,6-lupetidine, 3,5-lupetidine, diphenylamine, N-methylaniline, N-ethylaniline, dibenzylamine, methylbenzylamine, dinaphthylamine, pyrrole, indoline, indole and morpholine; secondary polyamines such as N,N'-dimethylethylenediamine, N,N'-dimethyl-1,2-diaminopropane, N,N'-dimethyl-1,3-diaminopropane, N,N'-dimethyl-1,2-diaminobutane, N,N'-dimethyl-1,3-diaminobutane, N,N'-dimethyl-1,4-diaminobutane, N,N'-dimethyl-1,5-diaminopentane, N,N'-dimethyl-1,6-diaminohexane, N,N'-dimethyl-1,7-diaminoheptane, N,N'-diethylethylenediamine, N,N'-diethyl-1,2-diaminopropane, N,N'-diethyl-1,3-diaminopropane, N,N'-diethyl-1,2-diaminobutane, N,N'-diethyl-1,3-diaminobutane, N,N'-diethyl-1,4-diaminobutane, N,N'-diethyl-1,6-diaminohexane, piperazine, 2-methylpiperazine, 2,5-dimethylpiperazine, 2,6-dimethylpiperazine, homopiperazine, 1,1-di-(4-piperidyl)methane, 1,2-di-(4-piperidyl)ethane, 1,3-di-(4-piperidyl)propane, 1,4-di-(4-piperidyl)butane and tetramethylguanidine; tertiary amines such as trimethylamine, triethylamine, tri-n-propylamine, tri-iso-propylamine, tri-1,2-dimethylpropylamine, tri-3-methoxypropylamine, tri-n-butylamine, tri-iso-butylamine, tri-sec-butylamine, tripentylamine, tri-3-pentylamine, tri-n-hexylamine, tri-n-octylamine, tri-2-ethylhexylamine, tridodecylamine, trilaurylamine, tricyclohexylamine, dicyclohexylethylamine, monocyclohexyldiethylamine, N,N-dimethylhexylamine, N-methyldihexylamine, N,N-dimethylcyclohexylamine, N-methyldicyclohexylamine, triethanolamine, N,N-diethylethanolamine, N-ethyldiethanolamine, tribenzylamine, N,N-dimethylbenzylamine, diethylbenzylamine, triphenylamine, N,N-dimethylamino-p-cresol, N,N-dimethylaminomethylphenol, 2-(N,N-dimethylaminomethyl)phenol, N,N-dimethylaniline, N,N-diethylaniline, pyridine, quinoline, N-methylmorpholine, N-methylpiperidine and 2-(2-dimethylaminoethoxy)-4-methyl-1,3,2-dioxabornane; tertiary polyamines such as tetramethylethylenediamine, pyrazine, N,N'-dimethylpiperazine, N,N'-bis((2-hydroxy)propyl) piperazine, hexamethylenetetramine, N,N,N',N'-tetramethyl-1,3-butaneamine, 2-dimethylamino-2-hydroxypropane, diethylaminoethanol, N,N,N-tris(3-dimethylaminopropyl)amine, 2,4,6-tris(N,N-dimethylaminomethyl)phenol and heptamethylisobiguanide; various imidazoles such as imidazole, N-methylimidazole, 2-methylimidazole, 4-methylimidazole, N-ethylimidazole, 2-ethylimidazole, 4-ethylimidazole, N-butylimidazole, 2-butylimidazole, N-undecylimidazole, 2-undecylimidazole, N-phenylimidazole, 2-phenylimidazole, N-benzylimidazole, 2-benzylimidazole, 1-benzyl-2-methylimidazole, N-(2'-cyanoethyl)-2-methylimidazole, N-(2-cyanoethyl)-2-undecylimidazole, N-(2'-cyanoethyl)-2-phenylimidazole, 3,3-bis-(2-ethyl-4-methylimidazolyl) methane, adducts of alkylimidazoles with isocyanuric acid, and condensates of alkylimidazoles and formaldehyde; amidines such as 1,8-diazabicyclo[5.4.0]undecene-7, 1,5-diazabicyclo[4.3.0]nonene-5 and 6-dibutylamino-1,8-diazabicyclo[5.4.0]undecene-7, (2) quaternary ammonium salts of the amines in the above-mentioned paragraph (1) and halogens, mineral acids, Lewis acids, organic acids, silicic acid, boron tetrafluoride and the like, (3) complexes of the amines in the above-mentioned paragraph (1), borane and boron trifluoride, (4) phosphines such as trimethylphosphine, triethylphosphine, tri-iso-propylphosphine, tri-n-butylphosphine, tri-n-hexylphosphine, tri-n-octylphosphine, tricyclohexylphosphine, triphenylphosphine, tribenzylphosphine, tris(2-methylphenyl)phosphine, tris(3-methylphenyl)phosphine, tris(4-methylphenyl)phosphine, tris(diethylamino)phosphine, tris(4-methylphenyl) phosphine, dimethylphenylphosphine, diethylphenylphosphine, dicyclohexylphenylphosphine, ethyldiphenylphosphine, diphenylcyclohexylphosphine and chlorodiphenylphosphine, (5) mineral acids such as hydrochloric acid, sulfuric acid, nitric acid, phosphoric acid and carbonic acid, and half esters thereof, (6) Lewis acids typified by boron trifluoride and esterates of boron trifluoride, and (7) organic acids typified by carboxylic acids and half esters thereof.

Among these compounds, preferable examples which scarcely color the cured product include primary monoamines, secondary monoamines, tertiary monoamines, tertiary polyamines, imidazoles, amidines, quaternary ammonium salts and phosphines, and more preferable examples include secondary monoamines, tertiary monoamines, tertiary polyamines, imidazoles, amidines, quaternary ammonium salts and phosphines which have at most one group capable of reacting with an episulfide group. They may be used singly or in a mixture of two or more thereof. The above-mentioned curing catalyst can be used in an amount of 0.0001 mol to 1.0 mol per mol of a diepisulfide compound.

Furthermore, the novel episulfide compound of the present invention can be polymerized/cured with a compound having two or more functional groups capable of reacting with the episulfide group, a compound having one or more of these functional groups and one or more other homopolymerizable functional groups, or a compound having one functional group which can react with the episulfide group and which is further homopolymerizable, thereby preparing an optical material. Examples of the compound having two or more functional groups capable of reacting with the episulfide group include epoxy compounds, known episulfide compounds, polyvalent carboxylic acids, polyvalent carboxylic anhydrides, mercaptocarboxylic acids, polymercaptans, mercaptoalcohols, mercaptophenols, polyphenols, amines and amides. On the other hand, examples-of the compound having one or more functional groups capable of reacting with the episulfide group and having one or more other homopolymerizable functional groups include epoxy compounds having unsaturated groups such as a vinyl group, amromatic vinyl groups, a methacrylic group, an acrylic group and an allyl group, episulfide compounds, carboxylic acids, carboxylic anhydrides, mercaptocarboxylic acids, mercaptans, phenols, amines and amides.

Typical examples of the compound having two or more functional groups capable of reacting with the episulfide group are as follows.

Typical examples of the epoxy compounds include phenolic epoxy compounds obtained by the condensation of polyvalent phenol compounds such as hydroquinone, catechol, resorcin, bisphenol A, bisphenol F, bisphenol sulfones, bisphenol ethers, bisphenol sulfides, halogenated bisphenol A and novolak resins with the epihalohydrin; alcoholic epoxy compounds obtained by the condensation of polyvalent alcohol compounds such as ethylene glycol, diethylene glycol, triethylene glycol, polyethylene glycol, propylene glycol, dipropylene glycol, polypropylene glycol, 1,3-propanediol, 1,4-butanediol, 1,6-hexanediol, neopentyl glycol, glycerin, trimethylolpropane trimethacrylate, pentaerythritol, 1,3- and 1,4-cyclohexanediol, 1,3- and 1,4-cyclohexanedimethanol, hydrogenated bisphenol A, bisphenol A.ethylene oxide adduct and bisphenol A.propylene oxide adduct with the epihalohydrin; glycidyl ester-containing epoxy compounds obtained by the condensation of polyvalent carboxylic acid compounds such as adipic acid, sebacic acid, dodecadicarboxylic acid, dimer acids, phthalic acid, isophthalic acid, terephthalic acid, tetrahydrophthalic acid, methyltetrahydrophthalic acid, hexahydrophthalic acid, HET acid, nadic acid, maleic acid, succinic acid, fumaric acid, trimellitic acid, benzenetetracarboxylic acid, benzophenonetracarboxylic acid, naphthalenedicarboxylic acid and diphenyldicarboxylic acid with the epihalohydrin; amine-containing epoxy compounds obtained by the condensation of primary diamines such as ethylenediamine, 1,2-diaminopropane, 1,3-diaminopropane, 1,2-diaminobutane, 1,3-diaminobutane, 1,4-diaminobutane, 1,5-diaminopentane, 1,6-diaminohexane, 1,7-diaminoheptane, 1,8-diaminooctane, bis(3-aminopropyl) ether, 1,2-bis(3-aminopropoxy)ethane, 1,3-bis(3-aminopropoxy)-2,2'-dimethylpropane, 1,2-, 1,3- and 1,4-bisaminocyclohexane, 1,3- and 1,4-bisaminomethylcyclohexane, 1,3- and 1,4- bisaminoethylcyclohexane, 1,3- and 1,4-bisaminopropylcyclohexane, hydrogenated 4,4'-diaminodiphenylmethane, isophoronediamine, 1,4-bisaminopropylpiperadine, m- and p-phenylenediamine, 2,4- and 2,6-tolylenediamine, m- and p-xylenediamine, 1,5- and 2,6-naphthalenediamine, 4,4'-diaminodiphenylmethane, 4,4'-diaminodiphenyl ether and 2,2-bis(4,4'-diaminodiphenyl)propane, and secondary diamines such as N,N'-dimethylethylenediamine, N,N'-dimethyl-1,2-diaminopropane, N,N'-dimethyl-1,3-diaminopropane, N,N'-dimethyl-1,2-diaminobutane, N,N'-dimethyl-1,3-diaminobutane, N,N'-dimethyl-1,4-diaminobutane, N,N'-dimethyl-1,5-diaminopentane, N,N'-dimethyl-1,6-diaminohexane, N,N'-dimethyl-1,7-diaminoheptane, N,N'-diethylethylenediamine, N,N'-diethyl-1,2-diaminopropane, N,N'-diethyl-1,3-diaminopropane, N,N'-diethyl-1,2-diaminobutane, N,N'-diethyl-1,3-diaminobutane, N,N'-diethyl-1,4-diaminobutane, N,N'-diethyl-1,6-diaminohexane, piperazine, 2-methylpiperazine, 2,5- and 2,6-dimethylpiperazine, homopiperazine, 1,1-di(4-piperidyl)methane, 1,2-di(4-piperidyl)ethane, 1,3-di(4-piperidyl)propane and 1,4-di(4-piperidyl)butane with the epihalohydrin; epoxy compounds obtained by the epoxidation of alicyclic epoxy compounds such as 3,4-epoxycyclohexylmethyl-3,4-epoxycyclohexane carboxylate, vinylcyclohexane dioxide, 2-(3,4-epoxycyclohexyl-5,5-spiro-3,4-epoxy)cyclohexanemetadioxane and bis(3,4-epoxycyclohexyl) adipate; and unsaturated compounds such as cyclopentadiene epoxide, epoxidized soybean oil, epoxidized polybutadiene and vinylcyclohexene epoxide; and urethane-containing epoxy compounds obtained by the reaction of the above-mentioned polyvalent alcohols and phenolic compounds with diisocyanates and glycidol.

A typical example of the known episulfide compounds is an episulfide compound obtained by episulfiding a part or all of the epoxy groups of the above-mentioned epoxy compound.

Typical examples of the polyvalent carboxylic acids, the polyvalent carboxylic anhydrides, the polyphenols, the amines and the like include compounds previously enumerated as the materials which are the partners of the reaction with the epihalohydrin described in the paragraphs regarding the epoxy compounds.

Typical examples of the polymercaptans include straight-chain dimercaptan compounds such as 1,2-dimercaptoethane, 1,3-dimercaptopropane, 1,4-dimercaptobutane, 1,6-dimercaptohexane, bis(2-mercaptoethyl)sulfide, 1,2-[bis(2-mercaptoethylthio)]ethane; branched aliphatic polymercaptan compounds such as 2-mercaptomethyl-1,3-dimercaptopropane, 2-mercaptomethyl-1,4-dimercaptobutane, 2-(2-mercaptoethylthio)-1,3-dimercaptopropane, 1,2-bis[(2-mercaptoethylthio)]-3-mercaptopropane, 1,1,1-tris(mercaptomethyl)propane and tetrakismercaptomethylmethane; ester-containing aliphatic polymercaptan compounds such as ethylene glycol dithioglycolate, ethylene glycol dithiopropionate, 1,4-butanediol dithioglycolate, 1,4-butanedioldithiopropionate, trimethylolpropanetris(β-thioglycolate), trimethylolpropanetris(β-thioglycolate), pentaerythritoltetrakis(β-thioglycolate) and pentaerythritoltetrakis(β-thiopropionate); and alicyclic dimercaptan compounds such as 1,4-dimercaptocyclohexane, 1,3-dimercaptocyclohexane, 1,4-dimercaptomethylcyclohexane, 1,3-dimercaptomethylcyclohexane, 2,5-dimercaptomethyl-1,4-dithiane, 2,5-dimercaptoethyl-1,4-dithiane, 2,5-dimercaptomethyl-1-thiane and 2,5-dimercaptoethyl-1-thiane.

Typical examples of the mercaptoalcohols include 2-mercaptoethanol, 3-mercapto-1-propanol, 1-mercapto-2-propanol, 4-mercapto-1-butanol, 3-mercapto-2-butanol, 3-mercapto-1,2-propanediol, 2-mercapto-1,3-propanediol, 1,3-dimercapto-2-propanol, 2,3-dimercapto-1-propanol, 1-mercaptomethyl-1,1-dimethylolpropane, 1,1-bis(mercaptomethyl)-1-methylolpropane, mercaptomethyltris(hydroxymethyl)methane, bis(mercaptomethyl)bis(hydroxymethyl)methane, tris(mercaptomethyl)hydroxymethylmethane and 2-(2-mercaptoethylthio)ethanol.

Typical examples of the mercaptophenols include 4-mercaptophenol and 2-mercaptohydroquinone-4-hydroxy-4'-mercaptobiphenyl.

Typical examples of the mercaptocarboxylic acids include thioglycolic acid, 2-thiopropionic acid, 3-thiopropionic acid, thiolactic acid, mercaptosuccinic acid, thiomalic acid, N-(2-mercaptopropionyl)glycine, 2-mercaptobenzoic acid, 2-mercaptonicotinic acid and 3,3-dithioisobutyric acide.

Furthermore, typical examples of the compound having one or more functional groups capable of reacting with the episulfide group and having one or more other homopolymerizable functional groups will be enumerated hereinafter. Examples of the epoxy compound having an unsaturated group include vinylphenyl glycidyl ether, vinylbenzyl glycidyl ether, glycidyl methacrylate, glycidyl acrylate and allyl glycidyl ether. Examples of the episulfide compound having the unsaturated group include compounds obtained by episulfiding the epoxy groups of the above-mentioned epoxy compound having the unsaturated group, for example, vinylphenyl thioglycidyl ether, vinylbenzyl thioglycidyl ether, thioglycidyl methacryate, thiogrlycidyl acrylate and allyl thioglycidyl ether.

Examples of the carboxylic acid compound having the unsaturated group include α,β-unsaturated carboxylic acids such as acrylic acid, methacrylic acid, maleic acid, maleic anhydride and fumaric acid. Moreover, examples of the amides having the unsaturated group include amides of the above-mentioned α,β-unsaturated carboxylic acids.

Furthermore, typical examples of the preferable compound having one functional group which can react with the episulfide group and which is further homopolymerizable include compounds having one epoxy group or one episulfide group. More typical examples thereof include monoepoxy compounds such as ethylene oxide and propylene oxide, glycidyl esters of monocarboxylic acids such as acetic acid, propionic acid and benzoic acid, glycidyl ethers such as methyl glycidyl ether, ethyl glycidyl ether, propyl glycidyl ether and butyl glycidyl ether, monoepisulfide compounds such as ethylene sulfide and propylene sulfide, thioglycidyl esters having structures derived from the above-mentioned monocarboxylic acid and thioglycidol (1,2-epithio-3-hydroxypropane), and thioglycidyl ethers such as methyl thioglycidyl ether (1,2-epithiopropyloxymethane), ethyl thioglycidyl ether, propyl thioglycidyl ether and butyl thioglycidyl ether. Above all, the compound having one episulfide group is more preferable.

The novel episulfide compound of the present invention can be polymerized/cured in the presence of a curing polymerization catalyst with the compound having two or more functional groups capable of reacting with the episulfide group of the novel episulfide compound of the present invention, the compound having one or more of these functional groups and one or more other homopolymerizable functional groups, or the compound having one functional group which can react with the episulfide group and which is further homopolymerizable, thereby preparing a cured resin. As the curing catalyst, there can be used the above-mentioned amines, phosphines and acids. Typical examples thereof include those which have been enumerated above.

Furthermore, in using the compound having the unsaturated group, it is preferable to utilize a radical polymerization initiator as a polymerization promotor. The radical polymerization initiator may be any substance, so long as it can produce a radical by heating or irradiation with ultraviolet rays or electron beams. Examples of the radical polymerization initiator include known thermal polymerization catalysts, for example, peroxides such as cumyl peroxyneodecanoate, diisopropyl peroxydicarbonate, diallyl peroxydicarbonate, di-n-propyl peroxydicarbonate, dimyristyl peroxydicarbonate, cumyl peroxyneohexanoate, tert-hexyl peroxyneodecanoate, tert-butyl peroxyneodecanoate, tert-hexyl peroxyneohexanoate, tert-butyl peroxyneohexanoate, 2,4-dichlorobenzoyl peroxide, benzoyl peroxide, dicumyl peroxide and di-tert-butyl peroxide; hydroperoxides such as cumene hydroperoxide and tert-butyl hydroperoxide; azo-based compounds such as 2,2'-azobis(4-methoxy-2,4-dimethylvaleronitrile), 2,2'-azobis(2-cyclopropylpropionitrile), 2,2'-azobis(2,4-dimethylvaleronitrile), 2,2'-azobisisobutyronitrile, 2,2'-azobis(2-methylbutyronitrile), 1,1'-azobis(cyclohexane-1-carbonitrile), 1-[(1-cyano-1-methylethyl)azo]formamide, 2-phenylazo-4-toxi-2,4-dimethyl-valeronitrile-2,2'-azobis (2-methylpropane) and 2,2'-azobis(2,4,4-trimethylpentane), and known photopolymerization catalysts such as benzophenone, benzoinbenzoin methyl ether. Above all, preferable are the peroxides, the hydroperoxides and the azo compounds, and more preferable are the peroxides and the azo compounds, and most preferable are azo-based compounds such as 2,2'-azobis(4-methoxy-2,4-dimethylvaleronitrile), 2,2'-azobis(2-cyclopropylpropionitrile), 2,2'-azobis(2,4-dimethylvaleronitrile), 2,2'-azobisisobutyronitrile, 2,2-azobis(2-methylbutyronitrile), 1,1'-azobis(cyclohexane-1-carbonitrile), 1-[(1-cyano-1-methylethyl)azo]formamide, 2-phenylazo-4-methoxy-2,4-dimethylvaleronitrile, 2,2'-azobis(2-methylpropane) and 2,2'-azobis(2,4,4-trimethylpentane). They can all be used singly or in the form of a mixture thereof.

The amount of the radical polymerization initiator depends upon the components of the composition and the curing method, and so it cannot be decided in a wholesale way. Nevertheless, it is usually in the range of 0.01 to 5.0% by weight, preferably 0.1 to 2.0% by weight based on the total weight of the composition.

Furthermore, in polymerizing/curing the novel episulfide compound of the present invention to obtain the cured resin, it is, needless to say, possible to add additives such as a known antioxidant, ultraviolet light absorber and the like for the purpose of further improving the practicality of the obtained material. Moreover, a known external and/or internal mold release agent can be used or added, thereby improving the release properties of the obtained cured material from a mold. Examples of the internal mold release agent referred to herein include fluorine-containing nonionic surface active agents, silicon-containing nonionic surface active agents, alkyl quaternary ammonium salts, phosphoric acid esters, acidic phosphoric acid esters, oxyalkylene type acidic phosphoric acid esters, alkali metal salts of the acidic phosphoric acid esters, alkali metal salts of the oxyalkylene type acidic phosphoric acid esters, metal salts of higher fatty acids, esters of the higher fatty acids, paraffins, waxes, higher aliphatic amides, higher aliphatic alcohols, polysiloxanes and aliphatic amine ethylene oxide adducts.

When the novel episulfide compound of the present invention is polymerized/cured to obtain the cured resin, there can be used the episulfide compound which is the raw material, and if necessary, the above-mentioned curing catalyst, glycidyl methacrylate or thioglycidyl methacrylate (in which the epoxy group of glycidyl methacrylate is episulfided) capable of reacting with the episulfide group having an unsaturated group and the like, but in this case, after additives such as a radical polymerization initiator, a radically polmerizable monomer, a mold release agent, an antioxidant and an ultraviolet light absorber are mixed, the polymerization/curing can be carried out by the following procedure to obtain an optical material such as a lens. That is to say, the mixture of the raw material is poured into a glass mold or a metal mold, and a polymerization/curing reaction is then advanced by heating. Afterward, the cured product is released from the mold to prepare the desired product. A curing time is usually in the range of 0.1 to 100 hours, preferably 1 to 48 hours, and a curing temperature is usually in the range of −10 to 160° C., preferably −10 to 140° C. Moreover, after the completion of the curing, the material may be subjected to an aneal treatment at a temperature of 50 to 150° C. for a period of 10 minutes to 5 hours, which is preferable to remove the strain of the optical material of the present invention. If necessary, a surface treatment for the impartment of hard coat, anti-reflection properties, anti-fogging properties or the like can further be carried out.

The preparation method of the optical material which is the cured resin regarding the present invention will be described in more detail. As described above, the main raw material is mixed with the secondary materials, and the resulting mixture is poured into a mold and then cured to prepare the optical material. In this case, the diepisulfide compound which is the main raw material may be mixed under stirring at one time with all of the suitably usable compound, i.e., the compound having two or more functional groups capable of reacting with the episulfide group, the compound having one or more of these functional groups and one or more other homopolymerizable functional groups, or the compound having one functional group which can react with the episulfide group and which is further homopolymerizable, and if necessary, a curing catalyst, a radical polymerization initiator, a mold release agent, a stabilizer and the like in one container, or the respective materials may stepwise be added and mixed, or several components are separately mixed and some resulting mixtures may be mixed again in one container. For the sake of the mixing, a temperature to be set, a time required for the mixing and the like should basically be such conditions as to sufficiently mix the components, but an excessive temperature and time cause some problems. For example, inconvenient reactions may occur among the materials and the additives, and the rise of viscosity may take place, which makes the casting operation difficult. The mixing temperature is in the range of about −10 to 100° C., preferably −10 to 50° C., more preferably −5 to 30° C. The mixing time is in the range of 1 minute to 5 hours, preferably 5 minutes to 2 hours, more preferably 5 minutes to 30 minutes, most preferably 5 minutes to 15 minutes or so. Before or after the mixing of the respective materials and additives, a degassing operation may be carried out under reduced pressure, and this operation is preferable to prevent the formation of air bubbles during the subsequent cast polymerization/curing.

At this time, the reduced pressure is in the range of about 0.1 to 700 mmHg, preferably about 10 to 300 mmHg. Furthermore, at the time of the pouring of the mixture, a microfilter or the like can be used to remove impurities and the like therefrom by filtration, which is preferable to further enhance the quality of the optical material according to the present invention.

According to the novel episulfide compound of the present invention, an optical resin material having a sufficiently high refractive index and a good balance between the refractive index and an Abbe's number can be obtained which have scarcely been attained so long as a compound based on a conventional technique is used as a raw material. That is to say, the novel episulfide compound of the present invention permits the reduction of the weight of the optical resin material, the reduction of its wall thickness and the remarkable decrease in its chromatic aberration.

Furthermore, the optical material obtained by polymerizing/curing the novel episulfide compound of the present invention can be used in various use applications, and it is particularly preferable as a lens material for spectacles.

Next, the present invention will be described in detail with reference to examples, but the scope of the present invention should not be limited to these examples. Incidentally, the physical properties of obtained polymers were measured by the following procedures.

Refractive index and Abbe's number: They were measured at 25° C. by the use of an Abbe's refractometer.

Specific gravity: It was measured at 25° C. by the use of an electron gravimeter, and then calibrated in a usual manner.

Heat resistance: A product having a Vicat softening point of 120° C. or more was represented by ◯, a product having a softening point of less than 120° C. and 80° C. or more was represented by Δ, and a product having a softening point of less than 80° C. was represented by X.

Strength: In accordance with a three-point bending test using an autograph, a product having a strain of 0.1 or more was represented by ◯, a product having a strain of less than 0.1 and 5 or more was represented by Δ, and a product having a strain of less than 0.05 was represented by X.

EXAMPLE 1

A solution of 170.3 g of 1,4-bis(mercaptomethyl)-benzene and 185.1 g of epichlorohydrin was cooled to 10° C., and 40 ml of methanol and an aqueous solution obtained by dissolving 0.4 g of an aqueous sodium hydroxide solution in 4 ml of water were added to the cooled solution, followed by stirring at this temperature for 1 hour. Afterward, an aqueous solution obtained by dissolving 80.0 g of sodium hydroxide in 80 ml of water was added thereto, while a solution temperature was maintained at about 0 to 10° C., followed by stirring for 3 hours at this temperature. Next, 200 ml of water was added to the reaction mixture, and extraction was carried out with 300 ml of toluene. The resulting toluene layer was dried over sodium sulfate, and the used solvent was distilled off to obtain 275.8 g (97% of a theoretical amount) of 1,4-bis(glycidylthiomethyl)benzene in the state of a colorless transparent liquid.

Next, in a flask equipped with a stirrer, a thermometer and a nitrogen introducing tube were placed 142.2 g of 1,4-bis(glycidylthiomethyl)benzene, 304.2 g of thiourea, 11.3 g of acetic anhydride and 1 l of toluene as well as 1 l of methanol as solvents, and reaction was then carried out at 30° C. for 9 hours. After the reaction, the reaction solution was extracted with toluene, and the resulting extract was washed with a 1% aqueous sulfuric acid solution and then water. Afterward, the excessive solvents were distilled off to obtain 141.5 g of a product. From the results of elemental analysis, mass spectrometry, NMR analysis and IR analysis, it was apparent that the thus obtained product was 1,4-bis(β-epithiopropylthiomethyl)benzene (yield=90%).

| Elemental analysis: | | |
|---|---|---|
| | Found | Calcd. |
| C | 53.30% | 53.46% |
| H | 5.91% | 5.77% |
| S | 40.50% | 40.78% |

Mass spectrum (EI): $M^+$ 314 (theoretical molecular weight=314)

Infrared absorption spectrum: 620 $cm^{-1}$ (stretching vibration of an episulfide ring)

$^1$H-NMR: 7.2 ppm (t, 1H) 7.0 ppm (m, 3H) 3.6 ppm (m, 2H) 3.1 ppm (m, 2H) 3.0 ppm (m, 2H) 2.7 ppm (m, 2H) 2.6 ppm (m, 2H) 2.2 ppm (m, 2H)

Furthermore, 0.5 part by weight of N,N-diethylethanolamine was blended with 100 parts by weight of the compound obtained above, and the blend was then poured into a mold comprising 2 glass plates having an adjusted thickness of 2 mm. Afterward, the blend was polymerized/cured at 80° C. for 5 hours to obtain an optical material. The refractive index, the Abbe's number and the specific gravity of the obtained optical material were measured, and the results are shown in Table 1.

EXAMPLE 2

The same procedure as in Example 1 was repeated except that 1,4-bis(mercaptomethyl)benzene was replaced with 1,4-bis(mercaptomethyl)cyclohexane, thereby obtaining 1,4-bis(β-epithiopropylthiomethyl)cyclohexane in a total yield of 80%.

| Elemental analysis: | | |
|---|---|---|
| | Found | Calcd. |
| C | 52.34% | 52.45% |
| H | 7.66% | 7.55% |
| S | 39.90% | 40.01% |

Mass spectrum (EI): $M^+$ 320 (theoretical molecular weight=320)

Infrared absorption spectrum: 620 $cm^{-1}$ (stretching vibration of an episulfide ring)

$^1$H-NMR:3.2–2.9 ppm (m, 10H) 2.7 ppm (m, 2H) 2.6 ppm (m, 2H) 2.2 ppm (m, 2H) 3.0 ppm (m, 2H) 1.9–0.9 ppm (m, 8H) 2.6 ppm (m, 2H) 2.2 ppm (m, 2H)

EXAMPLE 3

(in the general formula (2), Z=H, U=H, m=1 and n=0)

The same procedure as in Example 1 was repeated except that 1,4-bis(mercaptomethyl)benzene was replaced with 2,5-bis(mercaptomethyl)-1,4-dithiane, thereby obtaining 2,5-bis(β-epithiopropylthiomethyl)-1,4-dithiane in a total yield of 82%.

| Elemental analysis: | | |
|---|---|---|
| | Found | Calcd. |
| C | 40.33% | 40.41% |
| H | 5.77% | 5.65% |
| S | 53.79% | 53.94% |

Mass spectrum (EI): M$^+$ 356 (theoretical molecular weight=356)

Infrared absorption spectrum: 620 cm$^{-1}$ (stretching vibration of an episulfide ring)

$^1$H-NMR: 3.2–2.9 ppm (m, 14H) 2.7 ppm (m, 2H) 2.6 ppm (m, 2H) 2.2 ppm (m, 2H)

After polymerization/curing, the refractive index, the Abbe's number and the specific gravity of an obtained optical material were measured, and the results are shown in Table 1.

EXAMPLE 4

(in the general formula (2), Z=H, U=H, m=2 and n=0)

The same procedure as in Example 1 was repeated except that 1,4-bis(mercaptomethyl)benzene was replaced with 2,5-bis(mercaptoethyl)-1,4-dithiane, thereby obtaining 2,5-bis(β-epithiopropylthiomethyl)-1,4-dithiane in a total yield of 85%.

| Elemental analysis: | | |
|---|---|---|
| | Found | Calcd. |
| C | 43.55% | 43.71% |
| H | 6.39% | 6.29% |
| S | 49.81% | 50.01% |

Mass spectrum (EI): M$^+$ 384 (theoretical molecular weight=384)

Infrared absorption spectrum: 620 cm$^{-1}$ (stretching vibration of an episulfide ring)

$^1$H-NMR: 3.2–2.9 ppm (m, 14H) 2.7 ppm (m, 2H) 2.6 ppm (m, 2H) 2.2 ppm (m, 2H) 2.0 ppm (m, 4H)

After polymerization/curing, the refractive index, the Abbe's number and the specific gravity of the resulting optical material were measured, and the results are shown in Table 1.

EXAMPLE 5

(in the general formula (2), Z=H, U=H, m=1 and n=1)

The same procedure as in Example 1 was repeated except that 1,4-bis(mercaptomethyl)benzene was replaced with 2,5-bis(mercaptoethylthiomethyl)-1,4-dithiane, thereby obtaining 2,5-bis(β-epithiopropylthioethylthiomethyl)-1,4-dithiane in a total yield of 87%.

| Elemental analysis: | | |
|---|---|---|
| | Found | Calcd. |
| C | 40.19% | 40.29% |
| H | 6.05% | 5.92% |
| S | 43.70% | 53.79% |

Mass spectrum (EI): M$^+$ 476 (theoretical molecular weight=476)

Infrared absorption spectrum: 620 cm$^{-1}$ (stretching vibration of an episulfide ring)

$^1$H-NMR: 3.2–2.8 ppm (m, 22H) 2.7 ppm (m, 2H) 2.6 ppm (m, 2H) 2.2 ppm (m, 2H)

After polymerization/curing, the refractive index, the Abbe's number and the specific gravity of the resulting optical material were measured, and the results are shown in Table 1.

EXAMPLE 6

(in the general formula (2), Z=CH$_2$SE$_{PS}$, U=H, m=1 and n=0)

The same procedure as in Example 1 was repeated except that 1,4-bis(mercaptomethyl)-benzene was replaced with 2,3,5,6-tetrakis(mercaptomethyl)-1,4-dithiane, thereby obtaining 2,3,5,6-tetrakis(β-epithiopropylthiomethyl)-1,4-dithiane in a total yield of 82%.

| Elemental analysis: | | |
|---|---|---|
| | Found | Calcd. |
| C | 40.39% | 40.50% |
| H | 5.55% | 5.44% |
| S | 53.99% | 54.06% |

Mass spectrum (EI): M$^+$ 592 (theoretical molecular weight=592)

Infrared absorption spectrum: 620 cm$^{-1}$ (stretching vibration of an episulfide ring)

$^1$H-NMR: 3.3–2.9 ppm (m, 20H) 2.7 ppm (m, 4H) 2.6 ppm (m, 4H) 2.2 ppm (m, 4H)

After polymerization/curing, the refractive index, the Abbe's number and the specific gravity of the resulting optical material were measured, and the results are shown in Table 1.

Comparative Example 1

In Example 1, the same procedure as in Example 1 was repeated except that 1,4-bis(mercaptomethyl)-benzene was replaced with 2,5-bis(hydroxymethyl)-1,4-dioxane, thereby obtaining 2,5-bis(β-epithiopropyloxymethyl)-1,4-dioxane in a total yield of 52%. After polymerization/curing, the refractive index, the Abbe's number and the specific gravity of the resulting optical material were measured, and the results are shown in Table 1.

Comparative Example 2

In Example 1, the same procedure as in Example 1 was repeated except that 1,4-bis(mercaptomethyl)-benzene was replaced with 2,5-bis(hydroxyethyloxymethyl)-1,4-dioxane, thereby obtaining 2,5-bis(β-epithiopropyloxyethyloxymethyl)-1,4-dioxane in a total yield of 55%. After polymerization/curing, the refractive index, the Abbe's number and the specific gravity of the resulting optical material were measured, and the results are shown in Table 1.

Comparative Example 3

In Example 1, the same procedure as in Example 1 was repeated except that 162.3 g of 1,4-bis(glycidylthiomethyl) benzene was replaced with 50 g of thiourea. With regard to the resulting product, it was apparent from NMR spectra that the formula (2) had Z=H, U=H, m=1 and n=0, and a numerical ratio of S in X of the formula (1) was 30%, on the average, of the total of S and O constituting a three-membered ring. After polymerization/curing, the refractive index, the Abbe's number and the specific gravity of the resulting optical material were measured, and the results are shown in Table 1.

Comparative Example 4

A mixture of 48 parts by weight of 1,8-dimercapto-4-mercaptomethyl-3,6-dithiaoctane and 52 parts by weight of metaxylylene diisocyanate was blended with dibutyltin chloride as a curing catalyst in an amount of 0.1 part by weight with respect to 100 parts by weight of the mixture, and after the formation of a uniform solution, degassing was sufficiently carried out under a reduced pressure of 10 mmHg. Next, the solution was poured into a mold, and then polymerized/cured at 80° C. for 20 hours in an oven. The refractive index, the Abbe's number and the specific gravity of the resulting optical material were measured, and the results are shown in Table 1.

TABLE 1

| | Episulfide Compound | Refractive Index $N_D$ | Abbe's Number $\nu_D$ | Heat Resistance | Strength |
|---|---|---|---|---|---|
| Example 1 | 1,4-bis(β-epithio-propylthiomethyl)-benzene | 1.67 | 34 | ○ | ○ |
| Example 2 | 1,4-bis(β-epithio-propylthioethyl)-cyclohexane | 1.66 | 40 | ○ | ○ |
| Example 3 | 2,5-bis(β-epithio-propylthiomethyl)-1,4-dithiane | 1.70 | 36 | ○ | ○ |
| Example 4 | 2,5-bis(β-epithio-propylthioethyl)-1,4-dithiane | 1.69 | 37 | ○ | ○ |
| Example 5 | 2,5-bis(β-epithio-propylthioethyl-thiomethyl)-1,4-dithiane | 1.70 | 36 | ○ | ○ |
| Example 6 | 2,3,5,6-tetrakis-(β-epithiopropyl-thiomethyl)-1,4-dithiane | 1.70 | 36 | ○ | ○ |
| Comp. Ex. 1 | 2,5-bis(β-epithio-propyloxymethyl)-1,4-dioxane | 1.57 | 45 | X | X |
| Comp. Ex. 2 | 2,5-bis(β-epithio-propyloxyethyl-oxymethyl)-1,4-dioxane | 1.56 | 46 | X | X |
| Comp. Ex. 3 | Formula (2) had Z = H, U = H, m = 1 and n = 0, and number of S in X of Formula (3) was 30% of total of S and 0 on the average. | 1.63 | 42 | Δ | Δ |
| Comp. Ex. 4 | 1,8-dimercapto-4-mercaptomethyl-3,6-dithiaoctane/metaxylylene diisocyanate = 48/52 | 1.66 | 32 | X | ○ |

What is claimed is:

1. An episulfide compound having two or more moieties represented by the following formula

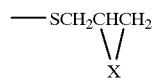

wherein X is S or O, and having a cyclic skeleton selected from the group consisting of (i) an alicyclic skeleton wherein the compound is selected from the group consisting of 1,3-bis(β-epithiopropylthio)cyclohexane, 1,4-bis(β-epithiopropylthio)cyclohexane, 1,3-bis(β-epithiopropylthiomethyl)cyclohexane, 1,4-bis(β-epithiopropylthiomethyl)cyclohexane, 2,5-bis(β-epithiopropylthio)-1,4-dithiane and 2,5-bis(β-epithiopropylthioethylthiomethyl)-1,4-dithiane;

(ii) an aromatic skeleton wherein the compound is selected from the group consisting of 1,3-bis(β-epithiopropylthio)benzene, 1,4-bis(β-epithiopropylthio)benzene, 1,3-bis(β-epithiopropylthiomethyl)benzene 1,4-bis(β-epithiopropylthiomethyl)benzene; and (iii) a heterocyclic skeleton including a sulfur atom as a heteroatom and the compound is represented by the formula

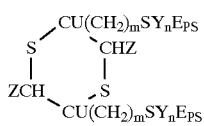

wherein Y is —(CH$_2$CH$_2$S), Z is a hydrogen atom, an alkyl group having 1 to 5 carbon atoms or —(CH$_2$)$_m$SY$_n$E$_{PS}$, U is a hydrogen atom or an alkyl group having 1 to 5 carbon atoms, m is an integer of 1 to 5, n is an integer of 0 to 4, and E$_{PS}$ is an epithiopropyl group of the formula

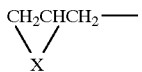

wherein X is S or O, and S is in an amount of 50% or more, on the average, of the total of S and O constituting a three-membered ring.

2. An optical material obtained by polymerizing/curing the episulfide compound described in claim 1.

3. The optical material according to claim 2 wherein the cyclic skeleton is an alicyclic skeleton and the compound is selected from the group consisting of 1,3-bis(β-epithiopropylthio)cyclohexane, 1,4-bis(β-epithiopropylthio) cyclohexane, 1,3-bis(β-epithiopropylthiomethyl) cyclohexane, 1,4-bis(β-epithiopropylthiomethyl) cyclohexane, 2,5-bis(β-epithiopropylthio-1,4-dithiane and 2,5-bis(β-epithiopropylthioethylthiomethyl)-1,4-dithiane.

4. The optical material according to claim 2 wherein the cyclic skeleton is an aromatic skeleton and the compound is selected from the group consisting of 1,3-bis(β-epithiopropylthio)benzene, 1,4-bis(β-epithiopropylthio) benzene, 1,3-bis(β-epithiopropylthiomethyl)benzene and 1,4-bis(β-epithiopropylthiomethyl)benzene.

5. The optical material according to claim 2 wherein the cyclic skeleton is a heterocyclic skeleton including a sulfur atom as a heteroatom and the compound is represented by the formula

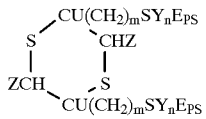

wherein Y is —(CH$_2$CH$_2$S), Z is a hydrogen atom, an alkyl group having 1 to 5 carbon atoms or —(CH$_2$)$_m$SY$_n$E$_{PS}$, U is a hydrogen atom or an alkyl group having 1 to 5 carbon atoms, m is an integer of 1 to 5, n is an integer of 0 to 4, and E$_{PS}$ is an epithiopropyl group of the formula

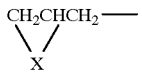

wherein X is S or O, and S is in an amount of 50% or more, on the average, of the total of S and O constituting a three-membered ring.

6. The optical material according to claim 5 wherein n is 0 to 3, m is 1 to 4, U is a hydrogen atom and Z is a hydrogen atom.

7. The optical material according to claim 6 wherein n is 0 to 2 and m is 1 to 4.

8. The optical material according to claim 6 wherein n is 0 and m is 1 to 3.

9. The optical material according to claim 6 wherein n is 0 and m is 1.

10. The optical material according to claim 6 wherein m is 2 and n is 0.

11. The optical material according to claim 6 wherein m is 1 and n is 1.

12. The optical material according to claim 5 wherein the compound is selected from the group consisting of 2,5-bis (β-epithiopropylthiomethyl)-1,4-dithiane, 2,5-bis(β-epithiopropylthioethylthiomethyl)-1,4-dithiane, 2,5-bis(β-epithiopropylthioethyl)-1,4-dithiane and 2,3,5-tri(β-epithiopropylthioethyl)-1,4-dithiane.

13. The optical material according to claim 5, wherein the compound is selected from the group consisting of

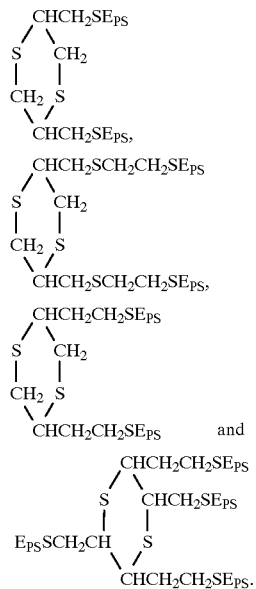

14. The optical material according to claim 5 wherein Z is CH$_2$SE$_{PS}$, U is H, m is 1 and n is 0.

15. The episulfide compound according to claim 1 wherein the cyclic skeleton is an alicyclic skeleton and the compound is selected from the group consisting of 1,3-bis (β-epithiopropylthio)cyclohexane, 1,4-bis(β-epithiopropylthio)cyclohexane, 1,3-bis(β-epithiopropylthiomethyl)cyclohexane, 1,4-bis(β-epithiopropylthiomethyl)cyclohexane, 2,5-bis(β-epithiopropylthio)-1,4-dithiane, and 2,5-bis(β-epithiopropylthioethylthiomethyl)-1,4-dithiane.

16. The episulfide compound according to claim 1 wherein the cyclic skeleton is an aromatic skeleton and the compound is selected from the group consisting of 1,3-bis (β-epithiopropylthio)benzene, 1,4-bis(β-epithiopropylthio) benzene, 1,3-bis(β-epithiopropylthiomethyl)benzene and 1,4-bis(β-epithiopropylthiomethyl)benzene.

17. The episulfide compound according to claim 1 wherein the cyclic skeleton is a heterocyclic skeleton including a sulfur atom as a heteroatom and the compound is represented by the formula

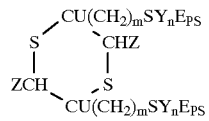

wherein Y is —(CH$_2$CH$_2$S), Z is a hydrogen atom, an alkyl group having 1 to 5 carbon atoms or —(CH$_2$)$_m$SY$_n$E$_{PS}$, U is a hydrogen atom or an alkyl group having 1 to 5 carbon atoms, m is an integer of 1 to 5, n is an integer of 0 to 4, and E$_{PS}$ is an epithiopropyl group of the formula

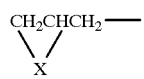

wherein X is S or O, and S is in an amount of 50% or more, on the average, of the total of S and O constituting a three-membered ring.

\* \* \* \* \*